United States Patent
Banisakher et al.

(10) Patent No.: US 10,949,622 B2
(45) Date of Patent: Mar. 16, 2021

(54) SYSTEMS AND METHODS FOR SEGMENTING DOCUMENTS

(71) Applicants: Deya Banisakher, Miami, FL (US); Naphtali Rishe, Miami Beach, FL (US); Mark Finlayson, North Bay Village, FL (US)

(72) Inventors: Deya Banisakher, Miami, FL (US); Naphtali Rishe, Miami Beach, FL (US); Mark Finlayson, North Bay Village, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 16/667,991

(22) Filed: Oct. 30, 2019

(65) Prior Publication Data

US 2020/0134024 A1 Apr. 30, 2020

Related U.S. Application Data

(60) Provisional application No. 62/752,751, filed on Oct. 30, 2018.

(51) Int. Cl.
| | |
|---|---|
| *G06F 40/30* | (2020.01) |
| *G06N 20/00* | (2019.01) |
| *G06F 40/205* | (2020.01) |
| *G16H 15/00* | (2018.01) |

(52) U.S. Cl.
CPC ............ *G06F 40/30* (2020.01); *G06N 20/00* (2019.01); *G16H 15/00* (2018.01); *G06F 40/205* (2020.01)

(58) Field of Classification Search
CPC ......... G06F 4/30; G06F 40/205; G16H 15/00; G06N 20/00
See application file for complete search history.

(56) References Cited

U.S. PATENT DOCUMENTS

| | | | | |
|---|---|---|---|---|
| 9,092,424 B2 * | 7/2015 | Nie | ....................... | G06F 40/295 |
| 2001/0032102 A1 * | 10/2001 | Gersing | ................ | G16H 70/40 |
| | | | | 705/2 |
| 2006/0041427 A1 * | 2/2006 | Yegnanarayanan | ..... | G10L 15/26 |
| | | | | 704/235 |

(Continued)

OTHER PUBLICATIONS

X. Wang and Z. Lu, "Extracting product features from online reviews based on two-level HHMM," 2014 Global Summit on Computer & Information Technology (GSCIT), Sousse, 2014, pp. 1-4, doi: 10.1109/GSCIT.2014.6970125.*

(Continued)

*Primary Examiner* — Fariba Sirjani
(74) *Attorney, Agent, or Firm* — Saliwanchik, Lloyd & Eisenschenk

(57) ABSTRACT

Systems and methods for automatically modeling the discourse structure of psychiatric reports and segmenting these reports into various sections are provided. The systems and methods can be based around a model that learns the section types, positions, and sequence and can automatically segment unlabeled text in a psychiatric report into the corresponding sections. Knowledge of the ordering of the sections can improve the performance of a section classifier and a text segmenter. A Hierarchical Hidden Markov Model (HHMM) can be trained and can categorize sections in psychiatric reports into a predefined section label.

20 Claims, 3 Drawing Sheets

*Family History: Her mother was depressed and was treated. Her mother is currently age 55 ... There is no family history of bipolar disorder, anxiety ... Medical history in the family is significant for her son, age 4, who is having seizures ... and several paternal great aunts had breast cancer.*

(56) References Cited

U.S. PATENT DOCUMENTS

| | | | | |
|---|---|---|---|---|
| 2006/0080309 | A1* | 4/2006 | Yacoub | G06K 9/00469 |
| 2006/0106795 | A1* | 5/2006 | Compton | G06Q 50/22 |
| 2008/0221863 | A1* | 9/2008 | Liu | G06F 40/53 |
| | | | | 704/2 |
| 2009/0099848 | A1* | 4/2009 | Lerner | G10L 17/26 |
| | | | | 704/271 |
| 2011/0078554 | A1* | 3/2011 | Nie | G06F 40/295 |
| | | | | 715/234 |
| 2011/0218796 | A1* | 9/2011 | Suzuki | G06F 40/40 |
| | | | | 704/2 |
| 2014/0236575 | A1* | 8/2014 | Tur | G06F 40/30 |
| | | | | 704/9 |
| 2016/0241669 | A1* | 8/2016 | Royon | H04L 67/2847 |
| 2016/0350483 | A1* | 12/2016 | Waldal | G16H 10/60 |
| 2017/0251985 | A1* | 9/2017 | Howard | A61B 5/165 |
| 2018/0373952 | A1* | 12/2018 | Bui | G06K 9/00456 |
| 2019/0228105 | A1* | 7/2019 | Ma | H04L 67/02 |

OTHER PUBLICATIONS

Lin-Yi Chou Techniques to incorporate the benefits of a hierarchy in a modified hidden Markov model COLING-ACL '06: Proceedings of the COLING/ACL on Main conference poster sessions•Jul. 2006 •pp. 120-127.*

Fine, Shai, Yoram Singer and Naftali Tishby, "The Hierarchical Hidden Markov Model: Analysis and Applications," Machine Learning, vol. 32, 1998, .COPYRGT. 1998 Kluwer Academic Publishers, pp. 41-62.*

* cited by examiner

*Family History:* Her mother was depressed and was treated. Her mother is currently age 55 ... *There is no family history of bipolar disorder, anxiety* ... *Medical history in the family is significant for her son, age 4, who is having seizures* ... *and several paternal great aunts had breast cancer.*

FIG. 1

```
Axis I    296.32   Major depressive disorder, recurrent, moderate
          305.00   Alcohol use disorder, mild
Axis II   V71.09   No diagnosis
Axis III           Hypertension
Axis IV            Problems with primary support group
Axis V    GAF = 48 (Current)
```

FIG. 2

| Parent Label | Section Label | # Words | # Sentences | Avg. Sent. Length | % Present | % Implicit |
|---|---|---|---|---|---|---|
| - | IDENTIFYING DATA | 12 | 2 | 6 | 100 | - |
| | CHIEF COMPLAINT | 27 | 3 | 9 | 100 | - |
| MEDICAL HISTORY | HISTORY OF PRESENT ILLNESS | 232 | 29 | 8 | 95 | 10 |
| | PSYCHIATRIC HISTORY | 85 | 8 | 11 | 82 | 36 |
| | SUBSTANCE ABUSE HISTORY | 98 | 10 | 10 | 88 | 44 |
| | REVIEW OF SYMPTOMS | 150 | 19 | 8 | 98 | 51 |
| | SURGERIES | 28 | 3 | 7 | 33 | - |
| - | ALLERGIES | 4 | 2 | 2 | 98 | - |
| | CURRENT MEDICATIONS | 40 | 9 | 4 | 100 | - |
| FAMILY HISTORY | BIRTH AND DEVELOPMENTAL HISTORY | 59 | 5 | 10 | 31 | 51 |
| | ABUSE HISTORY / TRAUMA | 110 | 9 | 12 | 79 | 34 |
| | FAMILY PSYCHIATRIC HISTORY | 44 | 5 | 9 | 73 | 80 |
| | FAMILY MEDICAL HISTORY | 48 | 7 | 7 | 92 | 38 |
| | SOCIAL HISTORY | 80 | 7 | 11 | 76 | 46 |
| | PREGNANCY | 29 | 3 | 8 | 47 | 64 |
| | SPIRITUAL BELIEFS | 12 | 2 | 5 | 24 | - |
| - | EDUCATION | 32 | 3 | 8 | 68 | - |
| | EMPLOYMENT | 31 | 3 | 9 | 79 | - |
| | LEGAL | 10 | 1 | 5 | 28 | - |
| MENTAL STATUS | MENTAL STATUS | 155 | 18 | 9 | 95 | 11 |
| | STRENGTHS AND SUPPORTS | 8 | 1 | 8 | 71 | 43 |
| | FORMULATION | 33 | 4 | 8 | 62 | - |
| - | DIAGNOSES | 63 | 12 | 5 | 100 | - |
| | PROGNOSIS | 8 | 2 | 3 | 74 | - |
| | TREATMENT PLAN | 121 | 12 | 10 | 100 | - |

FIG. 3

| Section | Independent Bigram | | | Flat HMM | | | HHMM | | |
|---|---|---|---|---|---|---|---|---|---|
| | P | R | $F_1$ | P | R | $F_1$ | P | R | $F_1$ |
| IDENTIFYING DATA | 0.83 | 0.81 | 0.82 | 0.96 | 0.94 | 0.95 | 0.98 | 0.95 | 0.97 |
| CHIEF COMPLAINT | 0.68 | 0.65 | 0.67 | 0.88 | 0.74 | 0.80 | 0.94 | 0.89 | 0.91 |
| MEDICAL HISTORY | 0.66 | 0.66 | 0.65 | 0.93 | 0.86 | 0.90 | 0.93 | 0.88 | 0.90 |
| HISTORY OF PRESENT ILLNESS | 0.69 | 0.67 | 0.68 | 0.91 | 0.86 | 0.88 | 0.94 | 0.86 | 0.90 |
| PSYCHIATRIC HISTORY | 0.65 | 0.60 | 0.62 | 0.74 | 0.85 | 0.79 | 0.93 | 0.86 | 0.89 |
| SUBSTANCE ABUSE HISTORY | 0.69 | 0.69 | 0.69 | 0.88 | 0.80 | 0.84 | 0.95 | 0.83 | 0.89 |
| REVIEW OF SYMPTOMS | 0.8 | 0.67 | 0.73 | 0.79 | 0.86 | 0.82 | 0.94 | 0.87 | 0.90 |
| SURGERIES | 0.4 | 0.31 | 0.35 | 0.79 | 0.51 | 0.62 | 0.85 | 0.64 | 0.73 |
| ALLERGIES | 0.6 | 0.80 | 0.69 | 0.90 | 0.86 | 0.88 | 0.88 | 0.91 | 0.89 |
| CURRENT MEDICATIONS | 0.87 | 0.74 | 0.80 | 0.90 | 0.84 | 0.87 | 0.91 | 0.93 | 0.92 |
| FAMILY HISTORY | 0.60 | 0.56 | 0.58 | 0.92 | 0.86 | 0.89 | 0.92 | 0.86 | 0.89 |
| BIRTH AND DEVELOPMENTAL HISTORY | 0.68 | 0.50 | 0.57 | 0.71 | 0.68 | 0.69 | 0.89 | 0.80 | 0.84 |
| ABUSE HISTORY / TRAUMA | 0.42 | 0.33 | 0.37 | 0.87 | 0.77 | 0.82 | 0.96 | 0.81 | 0.88 |
| FAMILY PSYCHIATRIC HISTORY | 0.57 | 0.59 | 0.58 | 0.92 | 0.87 | 0.89 | 0.92 | 0.90 | 0.91 |
| FAMILY MEDICAL HISTORY | 0.65 | 0.60 | 0.62 | 0.92 | 0.89 | 0.90 | 0.94 | 0.89 | 0.91 |
| SOCIAL HISTORY | 0.67 | 0.69 | 0.68 | 0.66 | 0.89 | 0.76 | 0.93 | 0.81 | 0.87 |
| PREGNANCY | 0.6 | 0.67 | 0.63 | 0.89 | 0.51 | 0.65 | 0.92 | 0.80 | 0.86 |
| SPIRITUAL BELIEFS | 0.73 | 0.46 | 0.56 | 0.90 | 0.9 | 0.90 | 0.93 | 0.88 | 0.90 |
| EDUCATION | 0.66 | 0.61 | 0.63 | 0.71 | 0.77 | 0.74 | 0.92 | 0.84 | 0.88 |
| EMPLOYMENT | 0.65 | 0.62 | 0.63 | 0.91 | 0.86 | 0.89 | 0.92 | 0.86 | 0.89 |
| LEGAL | 0.18 | 0.62 | 0.26 | 0.67 | 0.61 | 0.64 | 0.72 | 0.68 | 0.70 |
| MENTAL STATUS | 0.56 | 0.72 | 0.62 | 0.85 | 0.94 | 0.89 | 0.85 | 0.94 | 0.89 |
| MENTAL STATUS EXAM | 0.64 | 0.63 | 0.64 | 0.83 | 0.96 | 0.89 | 0.85 | 0.96 | 0.90 |
| STRENGTHS AND SUPPORTS | 0.42 | 0.82 | 0.56 | 0.80 | 0.92 | 0.86 | 0.82 | 0.92 | 0.87 |
| FORMULATION | 0.56 | 0.71 | 0.63 | 0.86 | 0.78 | 0.82 | 0.92 | 0.82 | 0.87 |
| DIAGNOSES | 0.88 | 0.76 | 0.81 | 0.96 | 0.95 | 0.96 | 0.98 | 0.98 | 0.98 |
| PROGNOSIS | 0.66 | 0.62 | 0.64 | 0.84 | 0.82 | 0.83 | 0.90 | 0.86 | 0.88 |
| TREATMENT PLAN | 0.74 | 0.83 | 0.78 | 0.95 | 0.93 | 0.94 | 0.97 | 0.93 | 0.95 |
| Macro-Average | 0.62 | 0.64 | 0.62 | 0.85 | 0.82 | 0.83 | 0.91 | 0.86 | 0.88 |
| Micro-Average | 0.62 | 0.62 | 0.62 | 0.86 | 0.83 | 0.84 | 0.93 | 0.91 | 0.92 |

FIG. 4

| # of Boundaries | Algorithm | $P_k$ | $W_d$ |
|---|---|---|---|
| System Choice | LCSeg | 0.29 | 0.37 |
| | TopicTiling | 0.27 | 0.33 |
| Provided | LCSeg | 0.25 | 0.33 |
| | TopicTiling | 0.20 | 0.25 |
| | HHMM | 0.20 | 0.26 |

FIG. 5

SYSTEMS AND METHODS FOR SEGMENTING DOCUMENTS

CROSS-REFERENCE TO A RELATED APPLICATION

This application claims the benefit of U.S. Provisional Application Ser. No. 62/752,751, filed Oct. 30, 2018, which is hereby incorporated by reference herein in its entirety, including any figures, tables, and drawings

BACKGROUND

With the exponential growth of free text in electronic health records (EHRs), which includes mental health documents, it is ever more important to develop natural language processing (NLP) models that automatically understand and parse such text. When incorporated in other systems, these models may aid: (1) clinical decision support; (2) the extraction of key population information and trends; and (3) precision medicine efforts where personalized information and trends are extracted and used in the treatment process.

The majority of clinical NLP work has focused on semantic parsing of clinical notes found in EHRs. There are several challenges in automatic understanding of unstructured text in EHRs, encompassing many levels of linguistic processing, including identifying document layouts, identifying document discourse organization, mapping lexical information to semantic concepts found in biomedical ontologies, and understanding inter-concept co-reference and temporal relations. These challenges are also present for mental health NLP applications.

A mental health assessment is the process through which a psychiatrist or a psychologist obtains and organizes necessary information about mental health patients. This process usually involves a series of psychological and medical tests (clinical and non-clinical), examinations, and interviews. These procedures serve the purpose of making a diagnosis that then guides a treatment or a treatment plan.

The output of a mental health assessment is a mental health report. Psychiatric reports are simpler subtypes of this document type, and mainly include long-form unstructured text. They are the end product of psychiatric assessments in which psychiatrists summarize the information gathered, as well as integrate the patient history, their evaluation, patient diagnosis, and suggested treatments or future steps.

BRIEF SUMMARY

Embodiments of the subject invention provide systems and methods to automatically model the discourse structure of psychiatric reports as well as segment these reports into various sections. The systems and methods can be based around a model that learns the section types, positions, and sequence and can automatically segment unlabeled text in a psychiatric report into the corresponding sections. Knowledge of the ordering of the sections can improve the performance of a section classifier and a text segmenter. A Hierarchical Hidden Markov Model (HHMM) can be trained and can categorize sections in psychiatric reports into a predefined section label (e.g., into one of 25 predefined section labels).

There are several types of psychiatric reports that vary depending on the type and purpose of assessment, including psychiatric evaluation reports, crisis evaluation reports, daily SOAP reports (Subjective, Objective, Assessment, Plan), mental status exam reports, and mini mental status exam reports. Embodiments of the subject invention focus on psychiatric reports (e.g., psychiatric evaluation reports). Although there is not a single strict format for psychiatric evaluation reports, there are general guidelines that psychiatrists follow when writing such reports. Drawing from the general psychiatric evaluation domains, these reports start with the patient's identifying information, followed by the patient's chief complaints, presenting illness and its history, personal and family medical history, mental status examination, and ending with the psychiatric medical diagnosis and treatment plan. This information is typically structured into an ordered list of headed sections. FIG. 3 shows a detailed list of the main sections of a psychiatric evaluation report in general order of appearance. Not all listed sections appear in all psychiatric evaluation reports, and they also do not necessarily appear in the same order, although there is usually a general pattern to the order.

Psychiatric evaluation reports represent a rich and still mostly-untapped source of information for developing systems for automatic diagnosis and treatment of mental health problems. These reports contain free-text structured within sections using a convention of headings. Embodiments of the subject invention can be based around a model for automatically detecting the position and type of different psychiatric evaluation report sections. The model has been developed using a corpus of 150 sample reports gathered from the Web and using sentences as a processing unit while section headings were used as labels of section type. From these labels a unified hierarchy of labels of section types was generated, and then $n$-gram models of the language found in each section were learned. To model conventions for section order, these $n$-gram models were integrated with an HHMM representing the probabilities of observed section orders found in the corpus, and then the HHMM n-gram model was used in a decoding framework to infer the most likely section boundaries and section types for documents with their section labels removed. The model was evaluated over two tasks—namely, identifying section boundaries and identifying section types and orders. The model significantly outperformed baselines for each task with an $F_1$ measure of 0.88 for identifying section types, and a 0.26 WindowDiff ($W_d$) and 0.20 $P_k$ scores, respectively, for identifying section boundaries.

BRIEF DESCRIPTION OF DRAWINGS

FIG. 1 shows an excerpt from a psychiatric report showing an example of implicitly including two different sections within another (i.e., Family Psychiatric History in the first underlined portion, and Family Medical History in the second underlined portion within Family History).

FIG. 2 shows an example of a DSM-IV multiaxal diagnosis assessment.

FIG. 3 shows a list of possible sections in a psychiatric report used in the corpus to develop the model of embodiments of the subject invention.

FIG. 4 shows section type identification results (precision, recall, and $F_1$ scores) per section, as well as micro and macro averages. Parent sections are in bold.

FIG. 5 shows section boundary identification results.

DETAILED DESCRIPTION

Embodiments of the subject invention provide systems and methods to automatically model the discourse structure of psychiatric reports as well as segment these reports into various sections. The systems and methods can be based around a model that learns the section types, positions, and sequence and can automatically segment unlabeled text in a psychiatric report into the corresponding sections. Knowledge of the ordering of the sections can improve the performance of a section classifier and a text segmenter. A Hierarchical Hidden Markov Model (HHMM) can be trained and can categorize sections in psychiatric reports into a predefined section label (e.g., into one of 25 predefined section labels).

The models of many embodiments of the subject invention were developed using a corpus of 150 sample reports gathered from the Web and using sentences as a processing unit while section headings were used as labels of section type. From these labels a unified hierarchy of labels of section types was generated, and then $n$-gram models of the language found in each section were learned. To model conventions for section order, these $n$-gram models were integrated with an HHMM representing the probabilities of observed section orders found in the corpus, and then the HHMM n-gram model was used in a decoding framework to infer the most likely section boundaries and section types for documents with their section labels removed. The model was evaluated over two tasks—namely, identifying section boundaries and identifying section types and orders. The model significantly outperformed baselines for each task with an $F_1$ measure of 0.88 for identifying section types, and a 0.26 WindowDiff ($W_d$) and 0.20 $P_k$ scores, respectively, for identifying section boundaries.

An aim of embodiments of the subject invention is to use an algorithm to build models that learn the section structure of a psychiatric evaluation report (or an evaluation psychiatric report). A psychiatric evaluation report includes several sections, often ordered in a usual way. Therefore, segmentation and classification, of blocks of unstructured text (at the sentence level) drawn from psychiatric evaluation reports into their appropriate section types, can be performed. The algorithm can assume that the reports follow the general guidelines of psychiatric evaluation report writing. Also, with the section labels removed from the reports, the segmentation task can be to find the section boundaries using sentences as the processing unit. This task is similar to topic shift detection in meeting minutes, newscasts, and doctor-patient counseling conversations (both written and spoken). Psychiatric reports are highly structured, with specific types of information (e.g., prescribed medications) found in particular sections (e.g., Treatment Plan), and with various general conventions for what information should appear in which sections, and in what order.

The algorithm comprises three subtasks: (1) learning and building a model for the sections' order and presence in a report; (2) learning and building models that describe the distinctive features of the various section types; and (3) applying a combination of these two models to simultaneously identify section boundaries and label section types. In the first subtask, the algorithm comprises building a two-level HHMM that models the positions and order of the sections of the reports. In the second subtask, the algorithm comprises building language models (namely, n-gram models) per section type that describe distinctive lexical information for each of those sections. The algorithm then couples the HHMM with the n-gram models where the HHMM and Hidden Markov Model (HMM) states represent the known section labels, while the observations of the states are the n-grams contained within each of the individual sections. In the third subtask, which is identifying section boundaries, the algorithm follows a decoding scheme using the Viterbi algorithm. That is, the Algorithm can comprise building an HHMM coupled with n-gram models, and the states of the HHMM represent the different sections of the reports, while the transition probabilities are obtained from the training dataset (i.e., the sections existence and order within the dataset). Various n-gram models can be built per section type (trained on the underlying dataset) and used as emission probabilities for the HHMM.

There are four important challenges in section classification of clinical notes and mental health reports. First, labels that psychiatrists use to designate sections are ambiguous and various; for example, a section titled Identification of Patient by one psychiatrist might be named Referral Data or Identifying Information by another. Second, psychiatrists often omit some sections entirely or include them implicitly within other sections or under other labels; for example, the section Childhood Events can be included in a larger section such as Family History while Strengths and Supports could be listed within Mental Status. FIG. 1 shows an example of including some sections within other sections. Third, the order of the sections can be different between different psychiatric reports. Fourth, some section labels may be omitted or skipped, especially if the information that would be placed in that section is not relevant to the particular patient being evaluated.

Additionally, with the section labels removed from the reports, the segmentation task can include finding the section boundaries using sentences as the processing unit. This task is similar to topic shift detection in meeting minutes, newscasts, and doctor-patient counseling conversations (both written and spoken). Though psychiatric reports are highly structured, with specific types of information (e.g., prescribed medications) found in particular sections (e.g., Treatment Plan), and with various general conventions for what information should appear in which sections and in what order, the segmentation task is not trivial as it faces the same aforementioned important challenges. Highly distinctive features must also be found to distinguish individual sentences (and thus, boundaries) in various sections as some of the sections can contain similar linguistic and structural features and may even contain similar topic keywords (e.g., language in Family Psychiatric History and Social History). The subtasks of this problem can be identified as" (1) learning and building a model for the order of sections and presence in a report; (2) learning and building models that describe the distinctive features of the various section types; and (3) applying a combination of these two models to simultaneously identify section boundaries and label section types.

Given the sequential nature of the sections of the reports, the ordering task can be treated as a sequence labeling task. That is, given a psychiatric report with n sections $S=(S_1, \ldots, S_n)$, determine the optimal sequence of section labels $O^*=(O_1^*, \ldots, O_n^*)$ among all possible section sequences. HMMs can be used successfully for sequence labeling in a wide variety of applications, including specifically natural language processing and medical informatics. HMM-based models can be coupled with section- or topic-specific n-gram models to segment text. Embodiments of the subject invention can take a supervised learning approach where the HMM parameters are learned using a labeled corpus.

To address the challenges outlined herein, a unified hierarchy of standardized section labels types was created, based on observations in a 150 report corpus that was assembled. Embodiments of the subject invention can focus on the sentence level. To model the inclusion of some sections within others, a two-level HHMM was built, in which some states contain HMM models for their implicit subsections.

This is in contrast to the approach attempted in certain related art methods that use a flat HMM, disregarding any hierarchy within the clinical notes sections. The HHMM model was first proposed as a strict tree structure where each state in the HHMM is an HHMM itself.

As discussed herein, to tackle the first subtask mentioned above a two-level HHMM was built that models the positions and order of the sections of the reports. To tackle the second subtask, language models (namely, n-gram models) were built per section type that describe distinctive lexical information for each of those sections. Then, the HHMM was coupled with the n-gram models where the HHMM and HMM states represent the known section labels, while the observations of the states are the n-grams contained within each of the individual sections. To tackle the third subtask, which is identifying section boundaries, a decoding scheme using the Viterbi algorithm was followed.

Embodiments of the subject invention simultaneously solve two problems within a psychiatric evaluation report: identifying section types; and identifying section boundaries. The first problem can be referred to as argumentative zoning (while the second is a type of text segmentation problem. Argumentative zoning refers to classifying text sections into mutually exclusive categories.

Embodiments of the subject invention detect the position and type of psychiatric report sections while improving upon earlier work on document analysis. A corpus of psychiatric documents was collected and a unified hierarchy of section labels was created. An n-gram-based HHMM model was built that successfully detects the order of sections as well as their boundaries within a given report. The model's performance was evaluated over two separate tasks (section ordering and section boundary identification), and it outperformed baselines for both of those tasks. This confirms that learning the section ordering of a psychiatric report yields better performance for boundary identification and text segmentation.

Embodiments include computer readable media (that can be in operable communication with one or more processors) that have instructions stored thereon that, when executed by a processor, perform steps of any of the models, algorithms, or methods (or any combination thereof) described herein.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

No known corpus of psychiatric reports annotated with section labels exists in the related art, so one was created. One hundred and fifty publicly available psychiatric evaluation report samples were collected by crawling the web through custom search engines (Google Custom Search Engine for Medical Transcriptionists and GoogleMT) and other sources (including http://www.medicaltranscription-samples.com/; http://mtsamples.com/; https://medword.com/psychiatry5.html; http://www.medicaltranscription-samplereports.com/; and http://onwe.bioinnovate.co/psychological-assessment-example/). The reports selected were complete and adhered to the general guidelines for psychiatric report writing discussed herein. Some of the reports were anonymized samples of real reports, while others were mock reports written for educational purposes. The corpus was prepared in two stages. First, the names of the labels were standardized by selecting a single uniform name for each section type and mapping corresponding section labels found in the corpus to those names. For example, some reports contained the section School while others listed it as Education. Here, Education was selected as the uniform section label across all reports. Second, a hierarchy was created for the section names, which reflected implicit embedded sections types that were found in the corpus. There were only three section types that included implicit subsections in the data—namely, Medical History, Family History, and Mental Status. For example, some reports containing the section Mental Status might in turn include information in that section about both Mental Status Exam and Strengths and Supports. In this case, these implicit subsection boundaries were identified (that is, the boundaries were not identified with a section header) and those subsections were labeled with both the parent and child label. FIG. 3 lists the parent sections that sometimes included other sections implicitly (first column), the unified list of section types found in the collected reports (second column), word and sentence level statistics (columns 3-5), and percentage of reports containing those sections in the corpus (last two columns). For both of these stages all 150 reports were used.

Following standard procedure for supervised machine learning, the corpus was split under a cross-validation paradigm into two sets for training and testing, where 80% of the reports were used in training and 20% for testing. This amounted to 120 and 30 reports for training and testing, respectively.

An HHMM was built where each state corresponds to a distinct section label. The terms state and parent state can be introduced when discussing the HHMM. A state is simply an HMM state corresponding to a distinct section. A parent state is an HHMM state corresponding to a collection of ordered sections. To account for sections listed implicitly, a two-level HHMM was created where parent states contained states representing the ordered subsections found in the parent state section. Thus, the model contained 25 states and three parent states corresponding to information in FIG. 3. The first HHMM layer contained both states and parent states, while the second layer contained a total of 12 states corresponding to the potential implicit subsections for the three parent states. In the HHMM, each parent state is simply an HMM itself. Thus, any mention of HMM parameter calculation for embodiments of the subject invention can apply to both states and parent states.

The model learned transition probabilities from the labeled corpus. The state transition probabilities capture constraints on section orderings. The probabilities between each state s were estimated using Equation 1. To account for sparsity (that is, unseen section orders) the probabilities were smoothed by the total number of section labels $t_S$ following Laplace smoothing.

$$P(s_j | s_i) = \frac{\text{count}(s_i, s_j) + 1}{\text{count}(s_i) + t_S} \quad (1)$$

The second level HMM models contained within the parent states follow the same scheme in probability estimation, but differ in the smoothing parameter ($t_S$). Here, the total number of section labels $t_S$ depends on the number of subsections in each of the parent states. For example, the parent state Medical History contains a total of four subsections or states, and thus its HMM model is smoothed by $t_S=4$. Then, all of the model's states were linked with empty transitions in addition to self-looping ones to account for missing sections as well as a section continuation, respectively (i.e., indicating a section shift or a continuation).

To tackle the second subtask identified above, n-gram language models (see Jain et al. (Jain, Khatri, and Indolia; Chunked n-grams for sentence validation; Procedia Computer Science, 57:209-213; 2015), which is hereby incorporated by reference herein in its entirety) were built that captured distinctive lexical information contained within the individual sections. This, in turn, helped classify unknown blocks of text (that is, text unseen previously by the trained models) within a report into their respective sections. Bigrams were used as the training corpus because higher n-gram models were extremely sparse, and had poor performance. Bigrams work well and better than others in most applications.

Independent bigram models were built for each section type in the reports, using only text from that section type. Tor each of the three section types represented by the parent states, bigram models were built using text found in all of the contained subsections. A common problem that arises with n-gram models is sparsity of phrases or words. This is especially the case when training on a small corpus. Given the relatively small corpus, the models were quite sparse at first, but Laplace Smoothing was used as a solution to this issue.

Similar to transition probabilities, the HHMM learned observation probabilities from the labeled corpus. A bigram model was trained for each state s of the HHMM. Equation 2 shows the computation for the likelihood of a sentence sequence $w_0^k$ (i.e., a long sequence of words) to be generated by a state s. Equation 3 shows the computation for estimating the specific state bigram probability along with Laplace smoothing counts for the corresponding section S ($V_S$ represents the vocabulary size for that section state).

$$P(w_0^k | s) = \prod_0^{k-1} P_s(w_{i+1} | w_i) \quad (2)$$

$$P_s(w_{i+1} | w_i) = \frac{\text{counts}(w_i^{i+1}) + 1}{\text{counts}(w_i) + |V_S|} \quad (3)$$

A rule-based approach was used to detect uniformly structured sections containing only standard medical terms such as medications and additional key terms. The sections mapped with hardcoded rules were the Current Medications and the standard DSM-IV multiaxal assessment contained within the Diagnosis section, one of which is illustrated in FIG. 2. This standard was dropped with the introduction of DSM-5 in 2013, but the dataset followed the older standard as most psychiatric reports in existence do because the new standard is relatively new.

For the Medications section, publicly available datasets containing lists of medications and the U.S. National Library of Medicine's Rx Norm dataset were used. String-matching was additionally used to locate the Diagnosis sections as the algorithm would search for the key headers "Axis I, II, III, IV, V". Generation of 26 bigram models was achieved, one for each section type (except for the two rule-based types) plus three parent section types.

The bigram models were integrated with the HHMM and then this bigram-HHMM model was used in a decoding framework to infer the most likely section boundaries and section types for documents with their section labels removed. The Viterbi algorithm was used and the following Equation 4 was applied to obtain the most likely labeling of sections O*, where n is the section index, and $k_n$ is the word index for section n:

$$O^* = \underset{s}{\arg\max} \; P(s) P\left(w_0^{k_n} \big| s\right) \quad (4)$$

$$= \underset{s_1 s_2 \cdots s_n}{\arg\max} P(s_1) P\left(w_0^{k_n} \big| s_1\right) \times \prod_{i=0}^{n} P(s_i | s_{i-1}) P\left(w_1^{k_n} \big| s_i\right)$$

Example 2

The corpus was randomly split into training and testing sets in a cross-validation setup, using ten folds, resulting in 120 reports for training and 30 for testing in each fold. The models were trained to learn a total of 25 distinct sections. There are two problems that the system can solve: 1) the section labeling problem applying the correct section type to each section; and 2) the section segmentation problem identifying the correct section boundaries. The system's performance was evaluated on these two problems separately.

For the section ordering, the performance of the model was evaluated on each section using the $F_1$ measure averaged across all folds. As for the boundary detection problem, the WindowDiff ($W_d$) and $P_k$ metrics were used. $W_d$ is described in Pevzner et al. (Pevzner and Hearst; A critique and improvement of an evaluation metric for text segmentation; Computational Linguistics, 28(1):19-36; 2002), and $P_k$ is described in Beeferman et al. (Beeferman, Berger, and Lafferty; Statistical models for text segmentation; Machine Learning, 34(1):177-210; 1999), both of which are hereby incorporated by reference herein in their entireties. These metrics ($W_d$ and $P_k$) compare the number of segmentation boundaries between a system's output and a gold standard by observing a scrolling window of text in the document, and run from 0 to 1, with scores closer to 0 being better. $W_d$ increases (gets worse) when the boundaries are different. Similarly, $P_k$ increases when a section type transition (i.e., a section type) is different. The $W_d$ score represents the probability that the number of boundaries found by the system is different from that in the gold standard, while the $P_k$ score represents the probability that any two sentences are incorrectly listed as being in the same section.

The system's performance in finding the correct labels of sections in a report was compared to two baseline methods. The first baseline method was introduced as a baseline by Li et al. (Li, Gorman, and Elhadad; Section classification in clinical notes using supervised hidden markov model; In Proceedings of the 1st ACM International Health Informatics Symposium IHI, pages 744-750, Arlington, Va.; 2010), which is hereby incorporated by reference herein in its entirety. This method uses bigrams to independently classify each section, disregarding any section order information. For the second baseline, the primary approach proposed by Li et al. was followed and is a flat HMM model that operates on a section level rather than a sentence level. Li's method ignores hierarchical information where some report sections are implicitly included within other sections. The implementation of this model included 25 states corresponding to each section within the reports. Both of these methods assume that the section boundaries are given, and as such they only generate a sequence labeling for section types.

Seg assumes that a topic change in written text occurs when chains of frequent repetitions of words begin and end. It rewards shorter chains over longer ones and further rewards chains with more repeated terms. The lexical cohesion between two chains is evaluated using a cosine similarity. The second method is TopicTiling, which is an augmentation of the well-known TextTiling algorithm. TopicTiling is LDA-based and represents segments as dense vectors of terms contained in dominant topics (as opposed to sparse term vectors).

For the section labeling problem, the model of embodiments of the subject invention equaled or outperformed both baselines in all the sections. FIG. 4 shows the precision, recall, and $F_1$ scores for the two baselines and the model. The Diagnosis section saw the best performance due to a rule-based approach. Similarly, Current Medications achieved high scores due to the use of dictionaries. All three models performed the worst in identifying the Legal section. This may be due to the low prevalence of this section and its content in the dataset. Similarly, sections with lower prevalence saw lower performance than others. Both baselines performed well in identifying the Identifying Data and Diagnosis sections due to their highly distinctive language. The model performed better for all implicit subsections, and significantly better for two (i.e., Pregnancy and Birth and Developmental History). The model performed exactly the same as the flat HMM baseline for the three parent types, as the model reduces to the flat HMM in these cases and because the flat HMM model assumes a fixed general ordering of the sections.

Because the report sections vary in size, both macro- and micro-averaged precision, recall, and F-measure (last two rows in FIG. 4) were computed. The model's micro-averaged F-measure is above 90%, which is significantly higher than both the flat-HMM and the independent bigram baselines performing at 85% and 62%, respectively. Similar to Li et al., both the model's HHMM and the flat-HMM baseline seemed to neither overfit nor underfit, which is indicated by higher micro-averaged scores compared to the macro-averaged scores.

Example 3

As for the boundary detection problem, two experiments were performed for the baselines because both baselines require a parameter representing the number of boundaries (number of topics minus one). In the first experiment, the parameter was allowed to be chosen by LCSeg and TopicTiling, respectively, while in the second experiment, the algorithms were provided with the correct number of boundaries (i.e., number of sections minus one). The model of embodiments of the subject invention, though, needs no prior information regarding the number of sections present in a given report. FIG. 5 shows the $W_d$ and $P_k$ scores for all three approaches. The subject system again outperformed both baselines indicated by lower $W_d$ and $P_k$ error rates overall. Both baselines performed better when the number of boundaries is known, and this is an expected result. In fact, TopicTiling outperformed the subject approach by a small margin when provided with the correct parameter value. However, when running open loop on new text, the number of sections will be unknown, so this result does not reflect how the approach would likely be used.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:
1. A computer-based system of segmenting a psychiatric evaluation report into sections, the system comprising:
   a processor; and
   a non-transitory computer-readable medium in operable communication with the processor and comprising program instructions stored thereon that, when executed, cause the processor to:
      receive text data of the psychiatric evaluation report;
      analyze the text data;
      learn and build a first model for an order and presence of the sections in the psychiatric evaluation report;
      learn and build a second model to describe distinctive features of the respective sections in the psychiatric evaluation report; and
      apply a combination of the first model and the second model to simultaneously identify boundaries of the respective sections and to label section types of the respective sections, thereby segmenting the psychiatric evaluation report, the first model being a Hierarchical Hidden Markov Model (HHMM), the sections comprising a medical history section, a family history section, a mental status section, a psychiatric history section, a family psychiatric history section, and a treatment plan section, the first model and the second model using sentences as processing units to identify the boundaries of the respective sections, and the first model and the second model requiring no prior information regarding a quantity of sections in the psychiatric evaluation report.

2. The system according to claim 1, the second model comprising a respective language model for each section type in the psychiatric evaluation report.

3. The system according to claim 2, each respective language model being an n-gram language model.

4. The system according to claim 3, the learning and building of the second model comprising using the n-gram language models as emission probabilities for the HHMM.

5. The system according to claim 1, the applying of the combination of the first model and the second model comprising following a decoding scheme using a Viterbi algorithm.

6. The system according to claim 5, the decoding scheme comprising applying the following equation to obtain the most likely labeling of each respective section, where O* is a set of the sections, n is an index of the sections, $w_0^{k_n}$ is a first long sequence of words, $w_1^{k_n}$ is a second long sequence of words, s is a state of the HHMM, $k_n$ is a word index for section n, and i is an index of the states of the HHMM:

$$O^* = \arg\max_s P(s) P(w_0^{k_n} | s)$$

$$= \arg\max_{s_1 s_2 \cdots s_n} P(s_1) P(w_0^{k_n} | s_1) \times \prod_{i=0}^{n} P(s_i | s_{i-1}) P(w_1^{k_n} | s_i)$$

7. The system according to claim 1, the learning and building of the first model comprising using states of the HHMM to respectively represent the sections in the psychiatric evaluation report.

8. The system according to claim 1, the program instructions, when executed, further causing the processor to train the system using preexisting psychiatric evaluation reports, the training comprising using training n-gram language models to capture distinctive lexical information contained within individual sections of the preexisting psychiatric evaluation reports, and the training being performed before the step of receiving the text data of the psychiatric evaluation report.

9. The system according to claim 8, the training n-gram language models being bigram language models.

10. The system according to claim 1, the program instructions, when executed, further causing the processor to classify unknown blocks of text, in the text data of the psychiatric evaluation report, into the respective sections.

11. A non-transitory computer-readable medium comprising program instructions stored thereon that, when executed, cause a processor to:

receive text data of a psychiatric evaluation report;

analyze the text data;

learn and build a first model for an order and presence of sections in the psychiatric evaluation report;

learn and build a second model to describe distinctive features of the respective sections in the psychiatric evaluation report; and apply a combination of the first model and the second model to simultaneously identify boundaries of the respective sections and to label section types of the respective sections, thereby segmenting the psychiatric evaluation report into the sections, the first model being a Hierarchical Hidden Markov Model (HHMM), the sections comprising a medical history section, a family history section, a mental status section, a psychiatric history section, a family psychiatric history section, and a treatment plan section, the first model and the second model using sentences as processing units to identify the boundaries of the respective sections, and the first model and the second model requiring no prior information regarding a quantity of sections in the psychiatric evaluation report.

12. The non-transitory computer-readable medium according to claim 11, the second model comprising a respective language model for each section type in the psychiatric evaluation report, and each respective language model being an n-gram language model.

13. The non-transitory computer-readable medium according to claim 12, the learning and building of the second model comprising using the n-gram language models as emission probabilities for the HHMM.

14. The non-transitory computer-readable medium according to claim 11, the applying of the combination of the first model and the second model comprising following a decoding scheme using a Viterbi algorithm.

15. The non-transitory computer-readable medium according to claim 14, the decoding scheme comprising applying the following equation to obtain the most likely labeling of each respective section, where O* is a set of the sections, n is an index of the sections, $w_0^{k_n}$ is a first long sequence of words, $w_1^{k_n}$ is a second long sequence of words, s is a state of the HHMM, $k_n$ is a word index for section n, and i is an index of the states of the HHMM:

$$O^* = \arg\max_s P(s) P(w_0^{k_n} | s)$$

$$= \arg\max_{s_1 s_2 \cdots s_n} P(s_1) P(w_0^{k_n} | s_1) \times \prod_{i=0}^{n} P(s_i | s_{i-1}) P(w_1^{k_n} | s_i)$$

16. The non-transitory computer-readable medium according to claim 11, the learning and building of the first model comprising using states of the HHMM to respectively represent the sections in the psychiatric evaluation report.

17. The non-transitory computer-readable medium according to claim 11, the program instructions, when executed, further causing the processor to train the first model using preexisting psychiatric evaluation reports, the training comprising using training n-gram language models to capture distinctive lexical information contained within individual sections of the preexisting psychiatric evaluation reports, and the training being performed before the step of receiving the text data of the psychiatric evaluation report.

18. The non-transitory computer-readable medium according to claim 17, the training n-gram language models being bigram language models.

19. The non-transitory computer-readable medium according to claim 11, the program instructions, when executed, further causing the processor to classify unknown blocks of text, in the text data of the psychiatric evaluation report, into the respective sections.

20. A computer-based system of segmenting a psychiatric evaluation report into sections, the system comprising:
   a processor; and
   a non-transitory computer-readable medium in operable communication with the processor and comprising program instructions stored thereon that, when executed, cause the processor to:
      train the system using preexisting psychiatric evaluation reports, the training comprising using first n-gram language models to capture distinctive lexical information contained within individual sections of the preexisting psychiatric evaluation reports;
      receive text data of the psychiatric evaluation report, the training of the system being performed before the receiving of the text data of the psychiatric evaluation report;
      analyze the text data;
      learn and build a first model for an order and presence of the sections in the psychiatric evaluation report;
      learn and build a second model to describe distinctive features of the respective sections in the psychiatric evaluation report;
      apply a combination of the first model and the second model to simultaneously identify boundaries of the respective sections and to label section types of the respective sections, thereby segmenting the psychiatric evaluation report; and
      classify unknown blocks of text, in the text data of the psychiatric evaluation report, into the respective sections, the first model being a Hierarchical Hidden Markov Model (HHMM),
   the second model comprising a respective second n-gram language model for each section type in the psychiatric evaluation report,
   the learning and building of the second model comprising using the second n-gram language models as emission probabilities for the HHMM,
   the applying of the combination of the first model and the second model comprising following a decoding scheme using a Viterbi algorithm,
   the decoding scheme comprising applying the following equation to obtain the most likely labeling of each respective section, where $O^*$ is a set of the sections, n is an index of the sections, $w_0^{k_n}$ is a first long sequence of words, $w_1^{k_n}$ is a second long sequence of words, s is a state of the HHMM, $k_n$ is a word index for section n, and i is an index of the states of the HHMM:

$$O^* = \arg\max_{s} P(s) P(w_0^{k_n} | s)$$
$$= \arg\max_{s_1 s_2 \cdots s_n} P(s_1) P(w_0^{k_n} | s_1) \times \prod_{i=0}^{n} P(s_i | s_{i-1}) P(w_1^{k_n} | s_i)$$

the learning and building of the first model comprising using the states of the HHMM to respectively represent the sections in the psychiatric evaluation report, and
   the first n-gram language models being bigram language models.

* * * * *